United States Patent
Fujimura et al.

(10) Patent No.: US 6,358,999 B2
(45) Date of Patent: Mar. 19, 2002

(54) USE OF ZINC TRANEXAMATE IN THE TREATMENT OF DIABETES

(75) Inventors: Hajime Fujimura, Kyoto; Masakatsu Nozaki, Gifu; Shun-ichi Tanaka, Yokohama; Reiko Natsuki, Yawata, all of (JP)

(73) Assignee: Hamari Chemicals, LTD, Osaka (JP)

( * ) Notice: Subject to any disclaimer, the term of this patent is extended or adjusted under 35 U.S.C. 154(b) by 0 days.

(21) Appl. No.: 09/799,692

(22) Filed: Mar. 7, 2001

(30) Foreign Application Priority Data

Mar. 8, 2000 (JP) ........................................ 2000-062880

(51) Int. Cl.⁷ ............................................. A61K 31/315
(52) U.S. Cl. ........................................ 514/494; 514/866
(58) Field of Search .................................. 514/494, 866

(56) References Cited

U.S. PATENT DOCUMENTS 5,506,264 A * 4/1996 Fujimura et al. ........... 514/494

* cited by examiner

*Primary Examiner*—Kevin E. Weddington
(74) *Attorney, Agent, or Firm*—Millen, White, Zelano & Branigan, P.C.

(57) ABSTRACT

A new use of a zinc tranexamate compound in the treatment of diabetes is disclosed. Oral administration of the compound adequately slows down absorption of glucose from digestive tracts by inhibiting α-glucosidase in vivo. The zinc tranexamate compound is also effective in the treatment of insulin-resistant type II diabetes.

6 Claims, 2 Drawing Sheets

USE OF ZINC TRANEXAMATE IN THE TREATMENT OF DIABETES

FIELD OF THE INVENTION

Figure 1:
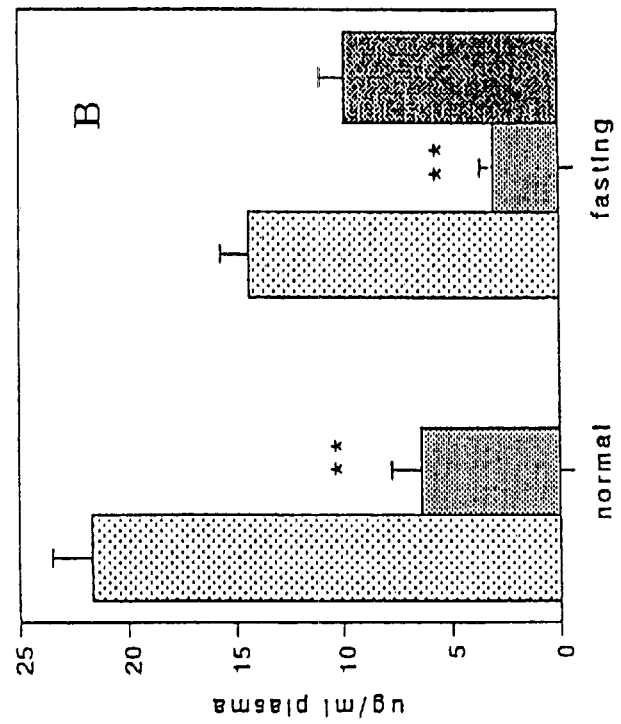

This invention relates to use of a zinc tranexamate compound in the treatment of diabetes. More particularly, it relates to use of a zinc tranexamate compound in the treatment of diabetes as an α-glucosidase inhibitor and also as a drug for treating insulin-resistant type II diabetes.

BACKGROUND OF THE INVENTION

In the past, it had been recommended to treat patients with type II diabetes by the diet and/or exercise therapy to control their blood sugar levels before starting drug therapy. Because the insulin-secreatory function of the patient gradually decreases as the disease proceeds, it is current practice to positively control the blood sugar level of the patients from the early stage of diabetes.

Known therapeutic agents for diabetes include insulin preparations and oral hypoglycemic agents such as sulfonyl ureas (SU). In addition, α-glucosidase inhibitors are of current interest in the treatment of diabetes α-Glucosidase is an enzyme which acts on poly- and oligosaccharides to hydrolyze into their constituent monosaccharides. Administration of an α-glucosidase inhibitor may delay the absorption of glucose through digestive tract by inhibiting the enzyme in vivo.

Known oral hypoglycemic drugs including SU may result in acute hypoglycemic conditions when an excessive dose is administered and exhibit a variety of their own adverse effects. Known α-glucosidase inhibitors may produce high incidence of gastrointestinal side effects and present, therefore, a number of problems upon long term administration. All of the above drugs are not effective in the treatment of insulin-resistant type II diabetes.

Antidiabetics in general are administered for a long term and thus require low incidence of adverse effects. A need exists for a new α-glucosidase-inhibiting antidiabetic drug which is safe and retards elevation of blood sugar level of diabetic patients after taking a meal without affecting their normal blood sugar levels by adequately delaying the absorption of glucose from digestive tracts. It is also desirable to provide a drug which is effective to treat insulin-resistant type II diabetes.

SUMMARY OF THE INVENTION

In one aspect, the present invention provides a method for the treatment of diabetes comprising orally administering a therapeutically effective amount of a zinc tranexamate compound to a patient with diabetes.

In another aspect, the present invention is directed to use of a zinc tranexamate compound in the manufacture of a medicament for treating diabetes in human subjects.

DETAILED DESCRIPTION OF THE INVENTION

Tranexamic acid, chemically trans-1-(aminomethyl) cyclohexanecarboxylic acid, is an antiplasminic hemostatic agent. Two moles of this acid form a stable salt with one atom of zinc, called "zinc tranexamate". The zinc salt, in turn, forms a water-soluble complex with a physiologically nontoxic organic acid such as acetic, glycolic, lactic, succinic, malic, tartaric, maleic or fumaric acid. As used herein, the term "zinc tranexamate compounds" includes zinc tranexamate either anhydrous or hydrated form and its complex with an organic acid.

Zinc tranexamate compounds were first synthesized and found to have antiinflammatory and antiulcerative activities by Fujimura et al. See, JP-B-0702524 and U.S. Pat. No. 5,506,264. It was not known, however, that either tranexamic acid or zinc tranexamate compounds are effective in the treatment of diabetes.

Suprisingly, we have discovered through a series of animal tests that zinc tranexamate compounds have a delaying effect on the absorption of glucose from digestive tracts by inhibiting α-glucosidase in vivo that leads to remarkable suppression of blood sugar levels in animals with experimental diabetes after loading the animals with a substrate sugar. We have also discovered that insulin resistance in rats with insulin-resistant type II diabetes was ameliorated by the oral administration of a zinc tranexamate compound. Details of the animal tests are given in the following examples in which zinc tranexamate monohydrate (Y-4) was used in the form of a suspension in 0.5% aqueous CMC solution unless otherwise indicated.

EXAMPLES

1. Suppresive effect of Y-4 on the elevation of blood sugar level after glucose loading Each group consisting of five mice was fasted for 17–24 hours and then Y-4 was orally administered at varying doses. After 30 minutes, mice were given glucose orally at a dose of 1 g/kg body weight. Blood samples were collected from the tail end of mice at different time intervals and assayed for blood sugar levels using GLUTEST™ sensor available from Matsushita Kotobuki Electronic Industry Company. Y-4 suppressed elevation of blood sugar level as shown in Table 1 below.

TABLE 1

Suppressive effect of Y-4 on the elevation of blood sugar level after glucose loading

| Dose (mg/kg) | Blood sugar level (mg/dl) | | | | |
|---|---|---|---|---|---|
| | 20 min. | 40 min. | 60 min. | 120 min. | 180 min. |
| Control | 64.8 ± 4.2 | 78.4 ± 3.0 | 74.9 ± 2.5 | 56.0 ± 1.5 | 50.8 ± 2.1 |
| 0 | 104.0 ± 1.1 | 127.6 ± 7.1 | 103.2 ± 3.3 | 73.6 ± 3.0 | 68.8 ± 6.1 |
| 50 | 96.0 ± 3.5 | 104.8 ± 7.1 | 99.0 ± 14.0 | 78.4 ± 6.4 | 58.4 ± 6.0 |
| 100 | 89.0 ± 2.9 | 112.6 ± 5.0 | 97.6 ± 0.9 | 73.1 ± 2.5 | 52.1 ± 1.9 |
| 200 | 83.0 ± 4.1 | 95.2 ± 3.6 | 84.4 ± 2.8 | 66.2 ± 3.3 | 53.9 ± 2.1 |

2. Suppressive effect of Y-4 on the elevation of blood sugar level after sucrose loading Each group consisting of five mice was fasted for 17–24 hours and then Y-4 was orally administered at varying doses.

Mice were orally given 1 g/kg body weight of sucrose 30 minutes after the administration of Y-4 or 2 g/kg body weight of sucrose 2 hours after the administration of Y-4. As in the preceding example, blood samples were collected from the tail end of mice at different time intervals and assayed for blood sugar levels. Table 2 shows the results of administration of the test compound 30 minutes before sucrose loading and Table 3 shows the results of administration of the test compound 2 hours before sucrose loading, respectively. A significant suppressive effect on the elevation of blood sugar level was observed in a dose responsive manner and delayed absorption of sucrose was demonstrated in groups given 100 mg/kg and 200 mg/kg of Y-4 30 minutes before sucrose loading up to 90 minutes after the sucrose loading as shown in Table 2. Similar results were obtained in the group given 200 mg/kg of Y-4 two hours before sucrose loading as shown in Table 3.

TABLE 2

Suppresive effect of Y-4 on the elevation of blood sugar level after sucrose loading (30 minutes before sucrose loading)

| Dose | Blood sugar level (mg/dl) | | | |
|---|---|---|---|---|
| (mg/kg) | 20 min. | 40 min. | 60 min. | 90 min. |
| Control | 40.4 ± 2.3 | 49.8 ± 1.7 | 52.9 ± 2.1 | 52.4 ± 3.0 |
| 0 | 79.0 ± 9.4 | 98.6 ± 7.4 | 93.2 ± 8.2 | 82.0 ± 5.0 |
| 50 | 71.0 ± 5.9 | 90.8 ± 10.0 | 76.6 ± 9.9 | 68.0 ± 8.1 |
| 100 | 50.8 ± 2.4* | 59.3 ± 2.4* | 72.9 ± 2.6 | 60.6 ± 2.3* |
| 200 | 40.4 ± 0.4** | 53.2 ± 7.5** | 58.2 ± 8.7* | 57.6 ± 3.2** |

*P < 0.05, **P < 0.01 relative to sucrose loading alone (zero dose)

TABLE 3

Suppressive effect of Y-4 on the elevation of blood sugar level after sucrose loading (2 hours before sucrose loading)

| Dose | Blood sugar level (mg/dl) | | | |
|---|---|---|---|---|
| (mg/kg) | 20 min. | 40 min. | 60 min. | 90 min. |
| Control | 53.2 ± 8.1 | 66.8 ± 16.7 | 80.6 ± 19.9 | 68.8 ± 19.8 |
| 0 | 102.2 ± 14.5 | 121.2 ± 16.1 | 142.8 ± 20.7 | 118.4 ± 10.5 |
| 200 | 66.2 ± 6.3* | 84.6 ± 8.9** | 94.0 ± 18.0* | 94.4 ± 17.2* |

*P < 0.05, **P < 0.01 relative to sucrose loading alone (zero dose)

3. Effect of Y-4 on blood sugar and insulin levels in mice having experimental diabetes after sucrose loading Experimental diabetes was induced in mice by treating the mice with streptozocin (STZ) (100 mg/kg/day i.p. for two days). After fasting for 17–24 hours, the mice were orally given Y-4 at varying doses 30 minutes before loading 2 g/kg of sucrose. After sucrose loading, blood samples were collected and assayed for blood sugar levels at different time intervals as in the preceding examples. The results are shown in Table 4. Administration of Y-4 30 minutes before sucrose loading remarkably suppressed the elevation of blood sugar level up to 3 hours.

TABLE 4

Suppressive effect of Y-4 on the elevation of sugar level in mice having experimental diabetes after sucrose loading

| Dose | Blood sugar level (mg/dl) | | | | |
|---|---|---|---|---|---|
| (mg/kg) | 20 min. | 40 min. | 60 min. | 90 min. | 180 min. |
| Control | 84.0 ± 3.9 | | | | |
| 0 | 178.8 ± 27.7 | 340.2 ± 40.0 | 329.4 ± 46.1 | 270.8 ± 34.2 | 284.9 ± 30.3 |
| 200 | 96.8 ± 10.3* | 134.2 ± 15.6** | 138.2 ± 15.6* | 137.0 ± 24.7* | 131.8 ± 25.6* |

*P < 0.05, **P < 0.01 relative to sucrose loading alone (zero dose)

Figure 2:
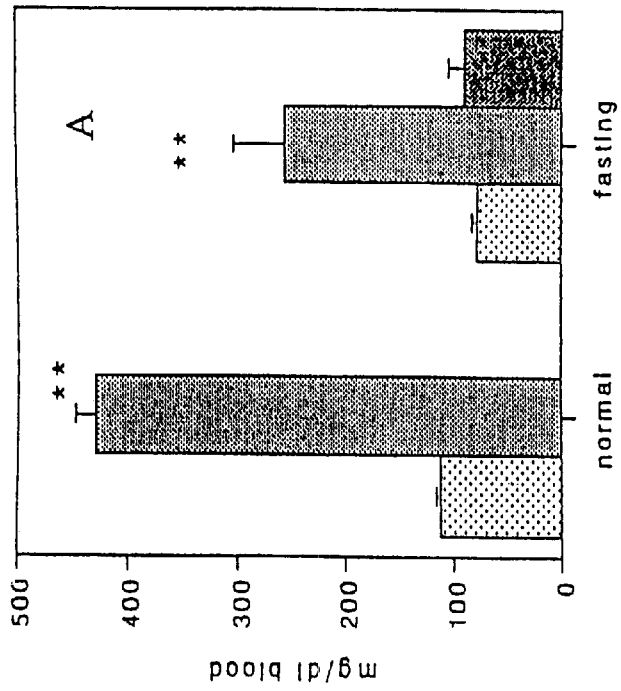

Similar to the above experiments, Y-4 was orally administered to the mice having experimental diabetes at a dose of 100 mg/kg 30 minutes before loading of 2 g of sucrose. Blood sugar and insulin levels in blood samples collected 30 minutes after sugar loading are shown in FIG. 1 and FIG. 2, respectively. Administration of Y-4 30 minutes before sucrose loading suppressed the elevation of blood sugar level almost completely whereas insulin level increased to a value which is not significantly different from the control value of normal mice group.

4. Inhibitory effect of Y-4 on intestinal α-glucosidase activity of normal mouse Intestinal tract enucleated from a normal mouse was homogenized by the conventional method after removing membrane mucosa. As a substrate, sucrose, starch, maltose or isomaltose was used. The homogenate was incubated with the substrate in the presence of a test compound (Y-4 or zinc chloride) at 37° C. for 30 minutes. The reaction mixture was centrifuged and the glucose concentration in the resulting supernatant was assayed. The glucose assay was conducted calorimetrically by adding a chromogenic reagent (0.47 mol/l of orthotoluidine, 16 mol/l of acetic acid, 10 mmol/l of boric acid) to the supernatant, heating the mixture in a boiling water bath for 8 minutes and measuring the absorbance at 635 nm. α-Glucosidase activity expressed in terms of glucose concentration/mg protein was calculated. The results are shown in Table 5 through Table 8 below. Y-4 inhibited α-glucosidase activity in the reaction with all substrates at a concentration higher than 5 mM in a dose responsive manner. Zinc chloride used for comparative purpose was as effective as Y-4 to inhibit the enzymatic reaction with sucrose but not effective with other substrates.

TABLE 5

Inhibition of glucose production from sucrose (normal mouse)

| Inhibitor concentration | Glucose (mg/mg protein) | |
|---|---|---|
| (mM) | $ZnCl_2$ | Y-4 |
| 0 | 5.239 ± 0.073 | 5.239 ± 0.073 |
| 5 | 3.509 ± 0.254 | 4.078 ± 0.073 |
| 10 | 1.658 ± 0.078 | 1.682 ± 0.097 |
| 30 | 0.714 ± 0.097 | 0.726 ± 0.157 |
| 50 | 0.133 ± 0.024 | 0.436 ± 0.036 |

TABLE 6

Inhibition of glucose production from starch (normal mouse)

| Inhibitor concentration | Glucose (mg/mg protein) | |
|---|---|---|
| (mM) | $ZnCl_2$ | Y-4 |
| 0 | 4.961 ± 0.000 | 5.264 ± 0.254 |
| 5 | 4.755 ± 0.109 | 4.211 ± 0.073 |
| 10 | 4.441 ± 0.182 | 3.400 ± 0.036** |
| 30 | 3.703 ± 0.532 | 1.162 ± 0.024** |
| 50 | 2.795 ± 0.085 | 0.339 ± 0.121** |

**P < 0.01 relative to $ZnCl_2$

TABLE 7

Inhibition of glucose production from maltose (normal mouse)

| Inhibitor concentration | Glucose (mg/mg protein) | |
|---|---|---|
| (mM) | $ZnCl_2$ | Y-4 |
| 0 | 23.026 ± 1.137 | 23.232 ± 0.230 |
| 5 | 19.917 ± 0.932 | 17.956 ± 0.423 |
| 10 | 18.114 ± 0.145 | 14.810 ± 0.956* |
| 30 | 15.657 ± 0.036 | 10.963 ± 0.399** |
| 50 | 10.442 ± 0.290 | 5.353 ± 0.017** |

*P < 0.05, **P < 0.01 relative to $ZnCl_2$

TABLE 8

Inhibition of glucose production from isomaltose (normal mouse)

| Inhibitor concentration | Glucose (mg/mg protein) | |
|---|---|---|
| (mM) | $ZnCl_2$ | Y-4 |
| 0 | 6.982 ± 0.085 | 6.933 ± 0.859 |
| 5 | 6.207 ± 0.230 | 5.009 ± 0.387 |
| 10 | 5.868 ± 0.496 | 4.150 ± 0.351* |
| 30 | 6.510 ± 0.169 | 3.473 ± 0.520** |
| 50 | 5.421 ± 0.339 | 3.158 ± 0.206** |

*$P < 0.05$, **$P < 0.01$ relative to $ZnCl_2$

5. Inhibitory effect of Y-4 on intestinal α-glucosidase activity of streptozocin-induced diabetic mouse Example 5 was repeated using intestinal tract enucleated from a diabetic mouse induced by the treatment with streptozocin instead of intestinal tract enucleated from a normal mouse to determine the inhibitory effect of Y-4 on α-glycosidase activity. The results are shown in Table 9 through Table 12 below. The intestinal α-glucosidase activity was higher in streptozocin-induced diabetic mouse than in normal mouse. Y-4 remarkably inhibited the enzyme in the reaction with all substrates. The inhibitory effect of Y-4 was more remarkable in the diabetic mouse than in normal mouse. $ZnCl_2$ used for comparative purpose showed only weak inhibitory effects.

TABLE 9

Inhibition of glucose production from sucrose (diabetic mouse)

| Inhibitor concentration | Glucose (mg/mg protein) | |
|---|---|---|
| (mM) | $ZnCl_2$ | Y-4 |
| 0 | 16.190 ± 1.174 | 16.129 ± 0.073 |
| 5 | 13.346 ± 0.411 | 10.128 ± 1.137 |
| 10 | 6.716 ± 0.145 | 5.312 ± 1.113 |
| 30 | 5.772 ± 0.121 | 3.146 ± 0.157 |
| 50 | 4.973 ± 0.024 | 2.251 ± 0.327 |

TABLE 10

Inhibition of glucose production from starch (diabetic mouse)

| Inhibitor concentration | Glucose (mg/mg protein) | |
|---|---|---|
| (mM) | $ZnCl_2$ | Y-4 |
| 0 | 16.021 ± 0.058 | 16.230 ± 0.093 |
| 5 | 12.240 ± 0.733 | 8.249 ± 0.419* |
| 10 | 9.191 ± 0.081 | 5.631 ± 0.151** |
| 30 | 10.204 ± 0.209 | 2.118 ± 0.175** |
| 50 | 8.866 ± 0.291 | 0.640 ± 0.070** |

*$P < 0.05$, **$P < 0.01$ relative to $ZnCl_2$

TABLE 11

Inhibition of glucose production from maltose (diabetic mouse)

| Inhibitor concentration | Glucose (mg/mg protein) | |
|---|---|---|
| (mM) | $ZnCl_2$ | Y-4 |
| 0 | 32.903 ± 0.058 | 32.682 ± 0.023 |
| 5 | 28.691 ± 1.222 | 23.060 ± 1.129 |
| 10 | 20.698 ± 0.442 | 18.569 ± 1.617* |
| 30 | 21.175 ± 0.105 | 15.113 ± 0.093** |
| 50 | 21.838 ± 0.652 | 12.793 ± 0.337** |

*$P < 0.05$, **$P < 0.01$ relative to $ZnCl_2$

TABLE 12

Inhibition of glucose production from isomaltose (diabetic mouse)

| Inhibitor concentration | Glucose (mg/mg protein) | |
|---|---|---|
| (mM) | $ZnCl_2$ | Y-4 |
| 0 | 6.003 ± 0.268 | 6.364 ± 0.303 |
| 5 | 5.945 ± 0.256 | 3.188 ± 0.035* |
| 10 | 5.038 ± 0.535 | 2.571 ± 0.233** |
| 30 | 5.794 ± 0.803 | 1.943 ± 0.047** |
| 50 | 6.027 ± 0.221 | 1.303 ± 0.430** |

*$P < 0.05$, **$P < 0.01$ relative to $ZnCl_2$

6. Improvement of insulin resistance in mice with type II diabetes

Figure 4:
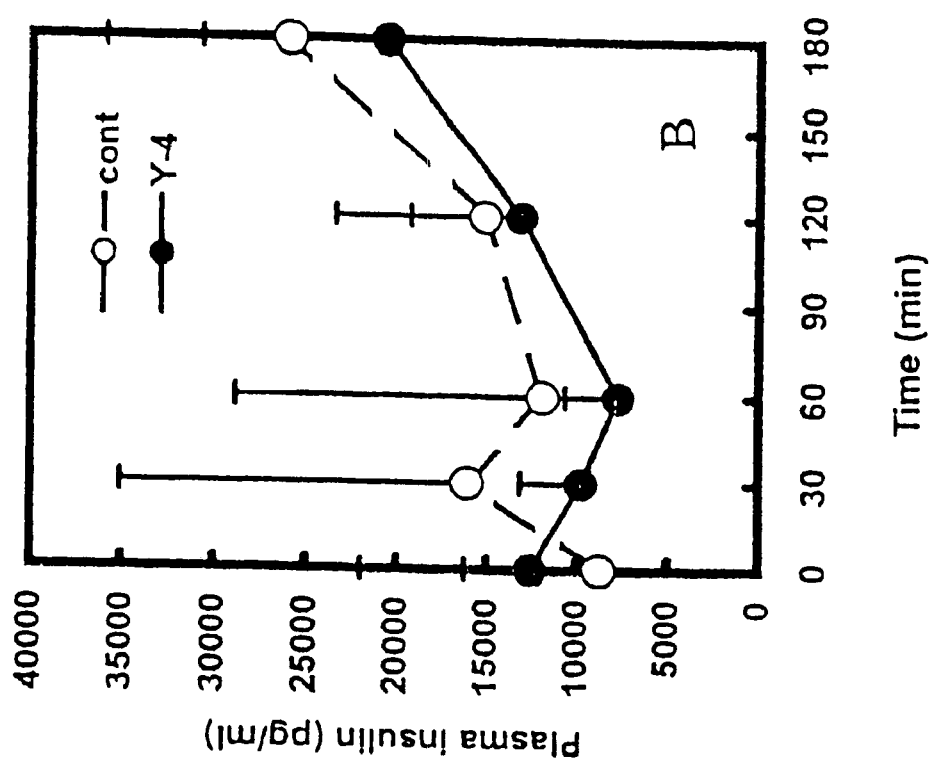
Figure 3:
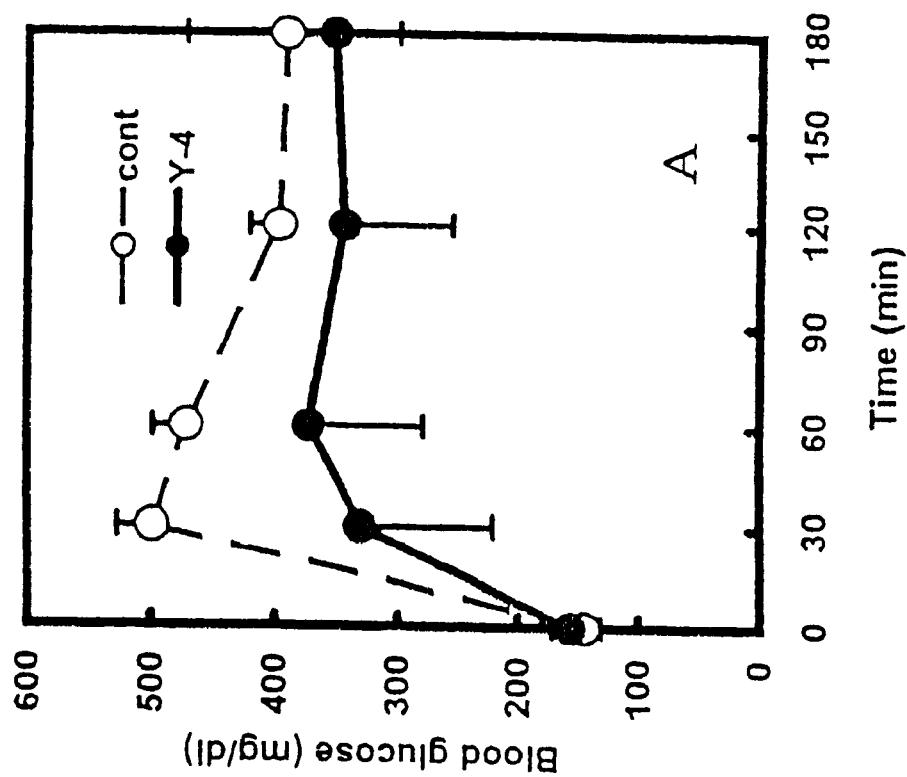

Y-4 was orally administered to male Wistar fatty rats (WFR) having tyep II diabetes with obesity and hyperlipidemia at an average daily dose of 150 mg/kg for consecutive 8 weeks. Eight weeks after the initiation of administration, the rats were fasted for 20 hours and then given oral administration of 2.5 g/kg/rat of glucose. Blood samples were collected from the tail vein at 30, 60, 120 and 180 minutes after the administration of glucose for assaying blood sugar and insulin levels. The results are shown in FIG. 3 and FIG. 4, respsectively. The blood sugar level was significantly controlled in the group treated with Y-4 as shown in FIG. 3 and the insulin level was normalized in the same group as shown in FIG. 4. This demonstrates that long term administration of Y-4 may improve the insulin resistance.

The acute toxicity of zinc tranexamate monohydrate (Y-4) is known to be very low since no death was observed in a toxicity test wherein 1,200 mg/kg of Y-4 was orally administered to mice. Other adverse effects are not known with respect to Y-4. Accordingly, the present invention provides an effective and highly safe treatment of diabetes by drug therapy for a long term.

Zinc tranexamate or monohydrate thereof may be orally administered either in the form of solid preparations such as tablets, granules, powders or capsules or in the form of liquid preparations such as syrups or other liquid preparations. Zinc tranexamate is known to form a water-soluble complex with a physiologically nontoxic organic acid such as acetic, glycolic, lactic, succinic, malic, tartaric maleic or fumaric acid. Liquid preparations may be formulated using this soluble complex. These solid and liquid preparations may be produced using the method well-known in the art by processing the active ingredient with a pharmaceutically acceptable carrier.

The dose may vary depending on the conditions of the disease, age and body weight of a particular patient and generally lies between 300 mg and 2,000 mg as zinc tranexamate per day for adult patients. This daily dose may be divided into 3 to 4 fractions for oral administration.

We claim:

1. A method for the treatment of diabetes comprising orally administering a therapeutically effective amount of a zinc tranexamate compound to a patient with diabetes.

2. A method according to claim 1 wherein said zinc tranexamate compound is selected from the group consisting of zinc tranexamate, monohydrate thereof, and a complex thereof with a physiologically nontoxic organic acid.

3. A method according to claim 1 wherein the diabetes is type II diabetes.

4. A method according to claim 1 wherein the diabetes is insulin-resistant type II diabetes.

5. A method according to claim 1 wherein the zinc tranexamate compound is administered in admixture with a pharmaceutical carrier for solid preparations.

6. A method according to claim 1 wherein the zinc tranexamate compound is administered in admixture with a pharmaceutical carrier for liquid preparations.

* * * * *